United States Patent
Utro et al.

(10) Patent No.: US 10,937,550 B2
(45) Date of Patent: Mar. 2, 2021

(54) PHYLOGENETIC TUMOR EVOLUTION TREES WITH DISTRIBUTION OF VARIANTS IN CELL POPULATIONS

(71) Applicant: International Business Machines Corporation, Armonk, NY (US)

(72) Inventors: Filippo Utro, Pleasantville, NY (US); Kahn Rhrissorrakrai, Woodside, NY (US); Laxmi Parida, Mohegan Lake, NY (US); Aldo Guzman Saenz, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 354 days.

(21) Appl. No.: 16/120,630

(22) Filed: Sep. 4, 2018

(65) Prior Publication Data

US 2020/0075170 A1     Mar. 5, 2020

(51) Int. Cl.
    *G16H 50/50*      (2018.01)

(52) U.S. Cl.
    CPC .................................. *G16H 50/50* (2018.01)

(58) Field of Classification Search
    None
    See application file for complete search history.

(56) References Cited

U.S. PATENT DOCUMENTS

2009/0292482 A1    11/2009    Frumkin

FOREIGN PATENT DOCUMENTS

WO    2014152990 A1    9/2014
WO    2017197351 A1    11/2017

OTHER PUBLICATIONS

SVEngine: An efficient and versatile simulator of genome structural variations with features of cancer clonal evolution Li Charlie Xia, Dongmei Ai, Hojoon Lee, Noemi Andor, Chao Li, Nancy R Zhang, Hanlee P Ji GigaScience, vol. 7, Issue 7, Jul. 2018 (Year: 2018).*
Bozic et al., "Quantifying Clonal and Subclonal Passenger Mutations in Cancer Evolution." PLOS Computational Biology, DOI:10.1371/journal.pcbi.1004731 Feb. 1, 2016, 1-19.

(Continued)

*Primary Examiner* — William C Trapanese
(74) *Attorney, Agent, or Firm* — Cantor Colburn LLP; Kristofer Haggerty

(57) ABSTRACT

A computer-implemented method includes inputting, to a processor, an N×K SSV frequency matrix M and an error tolerance δ≥0, wherein N is a number of SSVs and K is a number of time points, wherein matrix M comprises a plurality of time-resolved mutation frequencies for each SSV; clustering, by the processor, matrix rows in M that satisfy the δ to provide a plurality of SSV clusters; assigning, by the processor, a mean cluster frequency to each SSV within each SSV cluster; calculating errors for removing low frequency rows, for rounding rows to 1 or 0; assigning a root node for all SSV clusters of frequency 1; and calculating, by the processor, a δ-compliant time-series evolution tree with error ≤δ comprising the root node and a plurality time-stratified nodes, wherein calculating includes assigning a clonal configuration, optionally re-configuring the clonal configuration, and calculating error for re-configuring.

20 Claims, 11 Drawing Sheets

(56) References Cited

OTHER PUBLICATIONS

El-Kebir et al., "Reconstruction of clonal trees and tumor composition from multi-sample sequencing data." Bioinformatics, 31, 2015, i62-i70.
Jiang et al., "Assessing Intratumor Heterogeneity and Tracking Longitudinal and Spatial Clonal Evolutionary History by Next-Generation Sequencing." Proceedings of the National Academy of Sciences of the United States of America 113.37 (2016): E5528-E5537. PMC. Web. May 15, 2018.
List of IBM Patents or Patent Applications Treated As Related; Date Filed: Sep. 4, 2018, 2 pages.
Malikic et al., "Clonality inference in multiple tumor samples using phylogeny." Bioinformatics, vol. 31, Issue 9, May 1, 2015, pp. 1349-1356.
Manica et al., "Inferring clonal composition from multiple tumor biopsies," ARXIV, https://arxiv.org/abs/1701.07940. Jan. 2017.
Rhrissorrakrai et al., "Time-Series Phylogenetic Tumor Evolution Trees," U.S. Appl. No. 16/022,075, filed Jun. 28, 2018.
Utro et al., "Functional Analysis of Time-Series Phylogenetic Tumor Evolution Tree," U.S. Appl. No. 16/022,088, filed Jun. 28, 2018.

\* cited by examiner

| | | | | | |
|---|---|---|---|---|---|
| SSV1 | | 0.99 | 0.8 | 0.99 | 0.99 |
| SSV2 | | 0.808889 | 0.99 | 0.87 | 0.99 |
| SSV3 | | 0.808889 | 0.99 | 0.99 | 0.99 |
| SSV4 | | 0.808889 | 0.99 | 0.99 | 0.9 |
| SSV5 | | 0.808889 | 0.8 | 0.99 | 0.99 |
| SSV6 | | 0.80889 | 0 | 0 | 0 |
| SSV7 | | 0.23 | 0.28 | 0.24 | 0.29 |
| SSV8 | | 0.23 | 0.28 | 0.24 | 0.52 |
| SSV9 | | 0.23 | 0.28 | 0.43 | 0.52 |
| SSV10 | | 0.23 | 0 | 0 | 0 |
| SSV11 | | 0 | 0.28 | 0.24 | 0.29 |
| SSV12 | | 0 | 0.99 | 0 | 0 |
| SSV13 | | 0 | 0.8 | 0 | 0 |
| SSV14 | | 0 | 0.28 | 0.24 | 0.29 |
| SSV15 | | 0 | 0.28 | 0.24 | 0.52 |
| SSV16 | | 0 | 0.28 | 0.43 | 0.29 |
| SSV17 | | 0 | 0.28 | 0 | 0 |
| SSV18 | | 0 | 0 | 0.99 | 0 |
| SSV19 | | 0 | 0 | 0.43 | 0 |
| SSV20 | | 0 | 0 | 0.24 | 0 |
| SSV21 | | 0 | 0 | 0 | 0.99 |
| SSV22 | | 0 | 0 | 0 | 0.52 |
| SSV23 | | 0 | 0 | 0 | 0.29 |
| SSV24 | | 0 | 0 | 0 | 0 |

FIG. 2

ASSUMPTIONS:
1. FOR SSV r, A VARIANT IN A TUMOR SAMPLE
   a. R IS IRREVERSIBLE
   b. R IS UNIQUE
2. THE VARIANTS FOLLOW AN i.i.d. (UNIFORM) DISTRIBUTION

801

LEMMAS:
1. THERE EXISTS A CELL-POPULATION EVOLUTION REALIZATION OF A δ-COMPATIBLE TREE
2. FOR ANY FREQUENCY MATRIX M THERE ALWAYS EXISTS A δ-COMPATIBLE TREE FOR SOME δ ≥ 0
3. GIVEN FREQUENCIES $0 \leq a, b \leq 1$ FOR MUTATIONS A AND B, THE PROBABILITY OF NESTING, P(a,b) FOLLOWS A 0/1 LAW. THAT IS, A AND B ARE EITHER NESTED OR DISJOINT, BUT CANNOT STRADDLE

802

COROLLARY:
1. THE GREEDY ALGORITHM PRODUCES THE MAXIMUM LIKELIHOOD CONFIGURATION

PHYLOGENETIC TUMOR EVOLUTION TREES WITH DISTRIBUTION OF VARIANTS IN CELL POPULATIONS

BACKGROUND

The present invention generally relates to computing systems, and more specifically, to computer systems, computer-implemented methods, and computer program products configured to electronically implement phylogenetic tumor evolution trees that capture the distribution of variants in cell populations in the tumor.

Tumors include a plurality of distinct cell populations. Computerized massively parallel sequencing allows for the detection of somatic variants that correspond to cellular subpopulations in a tumor. Collections of somatic variants, such as single nucleotide polymorphisms (SNPs) or other variants, are referred to as clones. Phylogenetic clone trees, which are constructed by a computer processor from clonal analysis, thus represent evolutionary relationships among genetic cell lineages in the tumor.

SUMMARY

Embodiments of the present invention are directed to a computer-implemented method for determining a time series tumor evolution tree. A non-limiting example of the computer-implemented method includes inputting, to a processor, an N×K SSV frequency matrix M and a $\delta$, wherein $\delta \geq 0$ and is an error tolerance, wherein N is a number of SSVs, and wherein K is a number of time points. The matrix M includes a plurality of time-resolved mutation frequencies for each of the SSVs, wherein each mutation frequency is between 0 and 1. The SSVs, the time points and the frequencies are based on sequence data for a tumor from a subject, and at least one time-point represents an event in the subject's cancer treatment.

The method further includes clustering, by the processor, matrix rows in the matrix M that satisfy the $\delta$ to provide a plurality of SSV clusters, wherein each SSV cluster includes a plurality of SSVs with time-resolved mutation frequencies satisfying the $\delta$. The processor assigns a mean cluster frequency to each SSV within each SSV cluster in order to provide a first modified matrix M' including the mean cluster frequency for each SSV at each time point. The processor removes rows of the first modified matrix M' with cluster patterns across time points less than 1% to provide second modified matrix M", and the processor calculates an $Err_{rare}$, wherein $Err_{rare}$ is the error introduced by the removing operation.

The processor scans a second modified matrix M" and, for each row having one cell with a mean cluster frequency of 1, sets the entire row to 1, and calculates an $Err_{sweep}$, wherein $Err_{sweep}$ is the error introduced by setting rows to 1. The processor scans the second modified matrix M", and, for each row having one cell with a mean cluster frequency of 0, sets the entire row to 0, and calculates an $Err_{death}$, wherein $Err_{death}$ is the error introduced by setting rows to 1. The processor determines the maximum of $Err_{rare}$, $Err_{sweep}$, and $Err_{death}$ to provide $Err_{pre}$.

The processor assigns a root node for all SSV clusters of frequency 1 in the second modified matrix M". The processor calculates a $\delta$-compliant time-series evolution tree with an error $\leq \delta$ including the root node and a plurality time-stratified nodes, wherein the root node corresponds to time zero and each time-stratified node corresponds to a unique time point between 1 and K, by a process that includes: assigning, by the processor, for a time point j of the K time points, wherein $1 \leq j' < j$ and $j=1$ to K, a clonal configuration to each SSV cluster within time point j in second modified matrix M", wherein the clonal configuration for time point j has continuity with a clonal configuration for each SSV cluster within time point j' in second modified matrix M", and wherein the clonal configurations for time points j and j' do not include splitting of SSV clusters. The process by which the processor calculates a $\delta$-compliant time-series evolution tree further includes identifying, by the processor, a set of SSV clusters having a mean cluster frequency of 0 at time point j' and randomly selecting, by the computer, a subset of the SSV clusters having a mean cluster frequency of 0 at time point j'; and computing, by the processor, a re-configured clonal configuration for an error the clonal configurations for time points j and j' greater than $\delta$, and repeating, by the processor, until the $\delta$-compliant time-series evolution tree with an error $\leq \delta$ is determined, by the processor, from the re-configured clonal configuration, and calculating, by the processor, an $Err_j$ if a re-configured clonal configuration was computed; or computing, by the processor, the $\delta$-compliant time-series evolution tree from the clonal configurations for time points j and j' tree when the error $\leq \delta$; and calculating, by the processor, an $Error_{tree} = \max(Err_j, Err_{pre})$ for the $\delta$-compliant time-series evolution tree. The process finally includes outputting, by the processor, the $\delta$-compliant time-series evolution tree and corresponding $Error_{tree}$.

Embodiments of the invention are directed to computer program products and computer systems having substantially the same features of the computer-implemented method described above.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 2 depicts an input N×K SSV frequency matrix M for a plurality of SSVs according to an aspect of the invention;

FIG. 8 is a schematic of assumptions, lemmas and corollary of the model according to the embodiments of the invention;

Figure 1:
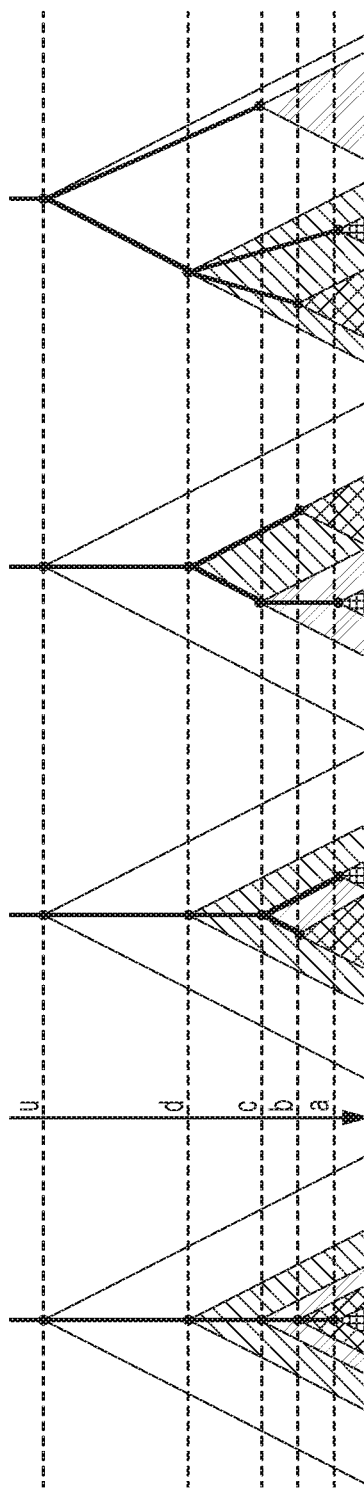
FIG. 1 is an illustration of the way four non-overlapping sets of SSVs can stack according to the computational methods of aspects of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example—"about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, phylogenetic clone trees have been constructed using computer analysis to represent evolutionary relationships among genetic cell lineages in a tumor. Typically, multiple samples from a patient's tumor are obtained, combined, and massively paralleled sequenced using computers. Clustering of variants is used to infer the clonal evolution of the tumor. Various computer-based methods have been developed for the construction of phylogenetic clone trees such as PyClone, PhyloWGS, ClonEvol, and others.

Several definitions are provided. A variant is defined as a change in the most common genetic sequence. Variants can include single nucleotide variants (SNVs), which are single nucleotide variations, and indels, which are insertions/deletions, typically of 1 to 50 bases. SNVs and indels are collectively referred to as simple somatic variations (SSVs). The cancer cell fraction (CCF) of a variant is the fraction of cells among all cancer cells with a particular variant. The variant allele frequency (VAF) is the relative frequency of a variant in a population, expressed as a fraction or percentage. The copy number variation (CNV) is when the number of copies of a particular gene varies.

As used herein, a clone is a collection of cells that are indistinguishable with respect to their SSVs. In other words, all the cells of a clone have the same set of SSVs.

An aspect that is missing from current phylogenetic evolution trees is the construction of phylogenetic trees that can be considered a valid tree in the context of likely populations of physical cells. For example, a tree that can simultaneously represent the explicit time-points at which samples were taken, the dynamic frequencies of the clones and phase changes of clonal populations can be used to identify the clones that grow and shrink in response to patient treatment. A tree that can accurately represent the likely dispersal of alterations within cell populations within the tumor would enable a more accurate assessment of the biological processes contributing to the disease or treatment phenotypes. This identification of accurate phylogenetic trees will enable the modification of patient treatments to either mitigate or stimulate these identified responses to improve patient outcomes.

Turning now to an overview of the aspects of the invention, one or more embodiments of the invention address the above-described shortcomings of the prior art by providing a method for constructing time series evolution trees that are compatible with a defined error tolerance δ.

The above-described aspects of the invention address the shortcomings of the prior art by enabling the construction of time series evolution trees that are compatible with a defined error tolerance δ. The time series tumor evolution trees according to aspects of the invention more accurately represent clones that map to physical cell populations. Unlike most phylogenetic trees, the δ-compliant time series trees described herein can be used to explicitly compare the cancer evolution to the sampled time points and the patient's treatment history. Such identification will enable the user to determine the timing for the next assay time given projected or similar trees and/or to detect the responder/non-responder status or the resistant/sensitive status of the tumor with respect to treatment.

Turning now to a more detailed description of aspects of the present invention, an implementation of methods performed by, e.g., a computer system 702 depicted in FIG. 7 according to embodiments of the invention will now be described.

Figure 7:
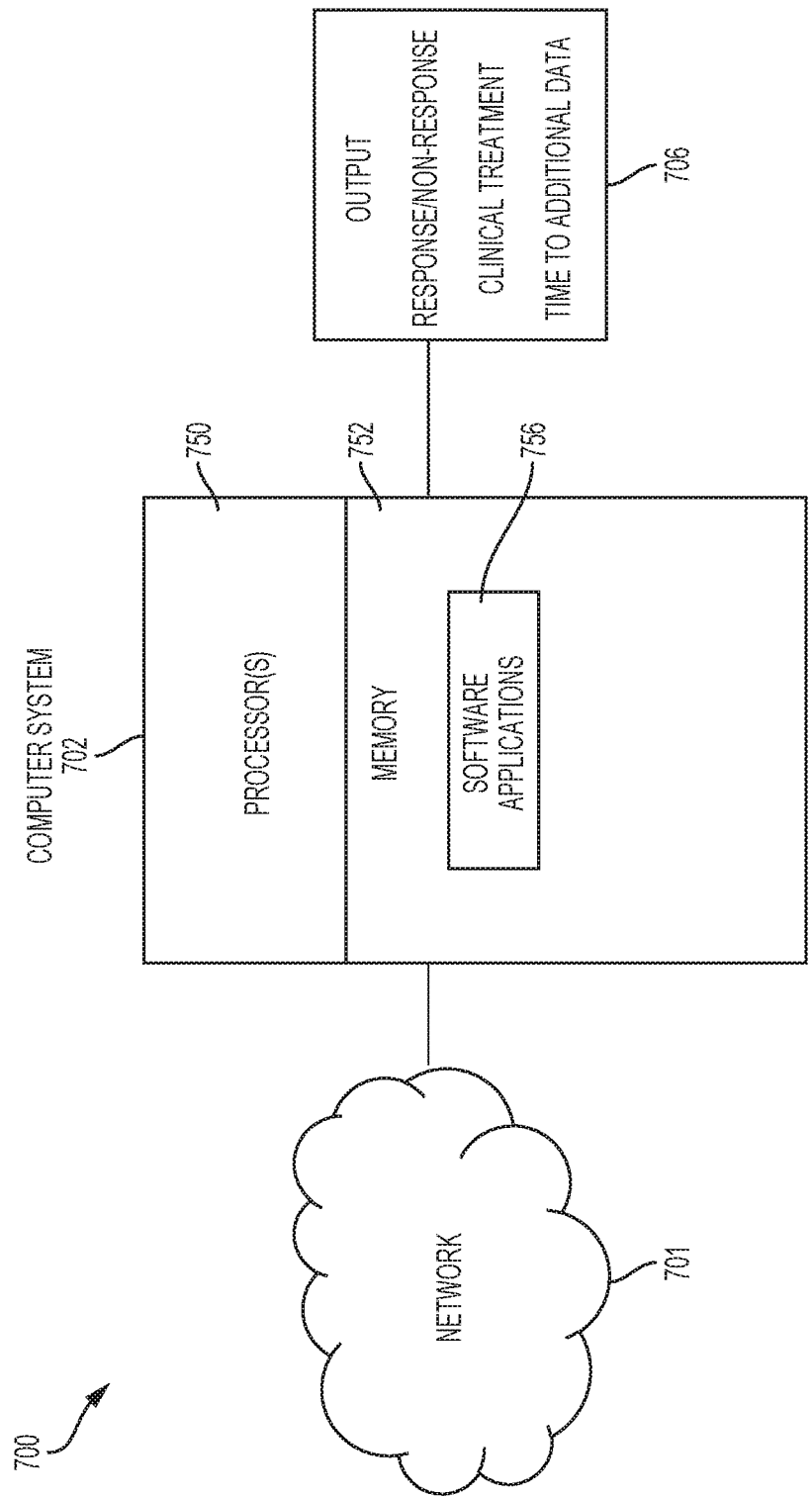
FIG. 7 illustrates a computer system for constructing a time series tumor evolution tree according to embodiments of the present invention.

More specifically, aspects of the computer-implemented method executed by the system 700 and software application 756 are illustrated in FIG. 7. An N×K SSV frequency matrix M and a δ 702 are inputted to processor 750. The δ-compliant time series tree is determined e.g., by processor 750 and software applications 756 depicted in FIG. 7. The tree can be used to determine outcomes 706 for the subject, for the subject.

The processor 750 executes the software application 756 (depicted in FIG. 7) which includes the model and optional assumptions. The input to the processor 750 in the method is a collection of SSVs and their frequency values (e.g., CCF) from a tumor from a subject at a plurality of time points. The input is specifically an N×K SSV frequency matrix M, wherein N is a number of SSVs and K is a number of time-points. FIG. 2 show an embodiment of a N×K SSV frequency matrix M 200. For example, if r is an SSV in a tumor sample, then the CCF value of r can be written as $0 \leq f(r) \leq 1$. The frequency can be expressed as either VAF or CCF, calculated at each time-point. In FIG. 2, for r=SSV1, the frequencies at times 1-4 are 0.99, 0.8, 0.99 and 0.99.

Aspects of the invention optionally includes several assumptions as detailed below and shown in FIG. 8.

As shown in FIG. 8, assumption 1 (801), if r is a mutation/variant in the tumor sample then r is:

1. irreversible, i.e., once the mutation occurs the reverse mutation of turning it back to its original state does not occur (i.e., no back mutation); and
2. unique, i.e., the same mutation does not occur elsewhere in the tumor (no parallel mutation).

As used herein, in addition to the frequency matrix M, a δ is inputted to the processor 750. δ is $\geq 0$ and is error tolerance which is set by the user. In an aspect, δ is 0.1 to 0.5. A minimal descriptor tree (MDT) for any matrix M and defined error tolerance δ is a δ-compatible time series tree that has the smallest number of leaf nodes In an N×K matrix M, $0 \leq M[i,t] \leq 1$ is the frequency value of SSV i at time point t. Each row i is a mutation label in the matrix. A δ-compatible time series tree is a labeled tree where each node v is labeled by $0 \leq v_f \leq 1$ and each edge e is labeled by a set, possibly empty, of mutations satisfying the following conditions:

1. M[i,t] maps to a node v of T with $|M[i,t]-v_f| \leq \delta$, wherein T is the set of all timepoints. Each mutation label i belongs to an edge label on a path from the root to v and belongs to no more than one edge label of T. That is, each SSV follows only one path from the root to subsequent nodes.
2. $v_f = \Sigma_i v_f^1$ must hold where $v^1$ is a child of v. That is, the sum of frequencies for a node cannot be more than the frequency of the parent.

3. The nodes are time-stratified, i.e., each node v maps to a unique time point $1 \leq t(v) \leq K$.
4. $T_k$ is the subgraph induced on T such that all nodes w of $T_k$ are such that t(w)=k. Then $\Sigma_{v \in R_k} v_f = 1.0$ where R is the set of root nodes of $T_k$. That is, for any given timepoint there are a set of subgraphs within that timepoint, however the subgraphs by necessity sum to 1 since at any given timepoint all cells of the tumor must be accounted for. For example when slicing the tree at a timepoint, there can be multiple roots, but the roots must sum to 1.

Note that a path from the root to a leaf node represents a clone. A node v with $v_f=0$ is a leaf node with $t(1) \leq t(v) \leq t(K)$.

Lemma 1 (802): There exists a cell-population evolution realization of a δ-compatible tree.

Lemma 2 (802): For any frequency matrix M there always exists a δ-compatible tree for some $\delta \geq 0$. That is, there always exists a tree, albeit possibly with a threshold $\delta' \geq \delta$.

As shown in FIG. 8, assumption 2 (801): The SSVs follow an i.i.d. (uniform) distribution, that is, the SSVs are independent and identically distributed.

Embodiments of the invention can also take into account disjointed or nested cell populations. The question of how multiple sets of SSVs stack up against each other is left completely to the computational method. For example, the possible ways the mutations can stack up as shown in FIG. 1. For example, let A, B, C, D be non-overlapping sets of SSVs such that their corresponding frequency values:

$$1.0 \geq u > d > c > b > a > 0.$$

The time axis is the molecular clock. For example, the structure on the extreme left of FIG. 1 suggests that there are cells with both A and B mutations while the other three suggest that there is no such cell. Currently, the multiple possible scenarios cannot be teased apart based on existing assay technologies.

Without loss of generality (WLOG) u=1.0.

Frequency values $0 \leq a,b \leq 1$ can be viewed as some subintervals of [0,1] A and B of lengths a and b respectively. Then in a cell-population realization either A and B are nested or disjoint (but cannot straddle).

Lemma 3. (802) Given $0 \leq a,b \leq 1$, the probability of nesting, P(a,b), follows a 0/1 law.

Proof: For non-trivial scenario, consider $0<a,b<1$. For $0<x<1$, as we have $\binom{n}{xn} \approx e^{nH(x)}$ where $H(x)=-x \log x-(1-x)\log(1-x)$ Then P(a,b) follows a 0/1 law as follows:

$$(1)\binom{n}{xn} \approx \frac{\binom{an}{bn}}{\binom{an}{bn}+\binom{(1-a)n}{bn}} \approx \frac{e^{anH(\alpha)}}{e^{anH(\alpha)}+e^{(1-a)nH(\beta)}} \to$$

$$\begin{cases} 0 & \text{if } aH(\alpha) < (1-p)H(\beta) \\ 1 & \text{if } aH(\alpha) > (1-p)H(\beta) \end{cases}$$

Where, $\alpha = \frac{b}{a}, \beta = \frac{b}{1-a}$.

Corollary 1. (803) The greedy algorithm produces the maximum likelihood configuration.

In an example according to embodiments of the invention, a methodology performed by processor 750 executing software application 756 proceeds as follows in steps 1 to 4. The output of the method is the tree and its error Err. Of particular note, Step 4(*a*) of the method of an aspect of the invention provides a convenient handle for replicates.

In the method, the input, to a processor 750, is a CCF matrix M and threshold δ≥0.

Let M[i,j] be mapped to node v of the δ-compatible tree. For instance, in one embodiment of the invention, the error can be defined as follows.

$$Err = \max_{i,j}(0, |M[i,j] - v_f| - \delta)$$

In an aspect of the invention the method then proceeds as follows.
1. Clustering: At each time point cluster the rows satisfying δ. Reassign the value of each element in the cluster to the mean of the cluster and update M to M'.
2. Preprocessing: Update M' to M" and $Err_{pre}$=max ($Err_{rare}$, $Err_{sweep}$, $Err_{death}$).
    (1) Remove the rows whose cluster patterns (across time points) are supported by about one percent of less of the SNPs. Compute $Err_{rare}$.
    (2) If M'[i,j] is 1.0, then the entire row is set to 1. Compute $Err_{sweep}$.
    (3) If M'[i,j] is 0.0, then all j'>j M'[i,j'] is set to zero. Compute $Err_{death}$.
3. Wrapper: This is the set of mutations that appear at frequency 1, or the root node. The wrapper continues at all time points unless a foreign progenitor or other exception is allowed. The root node is assigned an incoming edge with label with these mutations. If such mutations do not occur, then the label is an empty set. For root node v, the node label is set to 1.0.
4. Determine time series evolution trees: For j=1 to K: (let 1≤j'<j)
    (a) Using the Greedy algorithm, assign a clonal configuration to column j clusters, maintaining continuity with time points j'. Use the guiding principle of not splitting the clusters, to keep the size of δ-compatible tree minimal.
    Let B be the set of rows where M'[i,j'] is zero for all j'.
        i. Randomly select a subset of B to compute configuration. Backtrack to time j'<j if the error is greater than δ, and re-configure.
        ii. if B=∅, backtrack to time j'<j.
    (b)Compute $Err_j$ and update $Err_{j'}$, if backtracking was employed.
5. Err=max(max$_j$($Err_j$),$Err_{pre}$).

Figure 3:
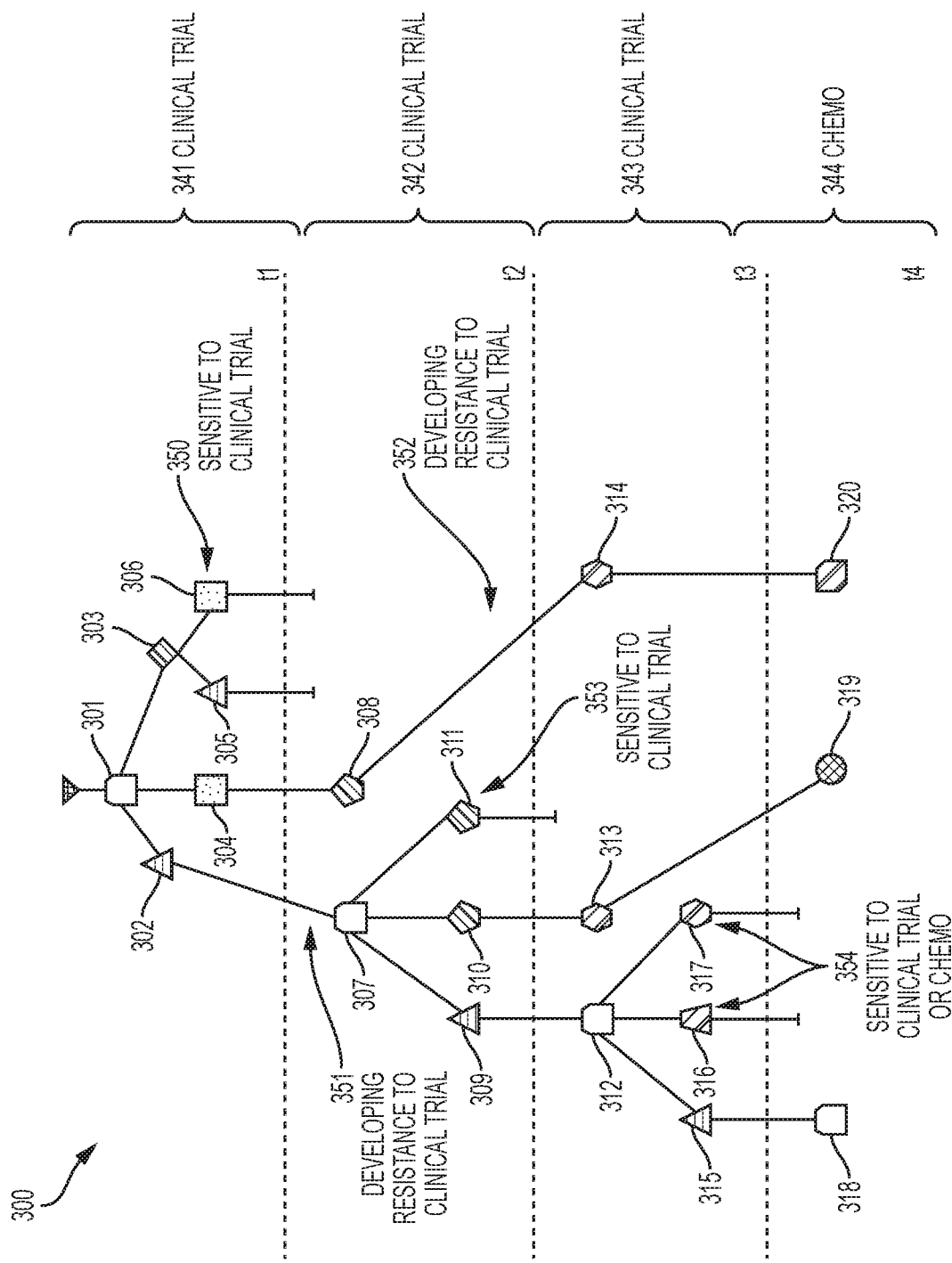
FIG. 3 depicts a tumor evolution tree with treatment information and likely points of resistance and sensitivity to treatments according to embodiments of the invention.

A processor 750 executes a software application 756 (depicted in FIG. 7) to create the δ-compliant time series tumor evolution tree 300 in FIG. 3, for example.

The model can optionally include a foreign progenator exception. For example, if a progenitor cell must come from the outside and not from the putative progenitor of the cells at the very first time point, then it is a foreign progenitor. For example, foreign progenitors can arise in metastasis. For example, if the sample data does not fit into the tree model as described, then it is likely that there is a foreign progenitor cell involved, perhaps from a metastatic event, and such foreign progenitor cells must be treated differently. The inventive method can thus help to identify cases where there is a foreign progenitor in the tumor sample.

EXAMPLE 1

Figure 4:
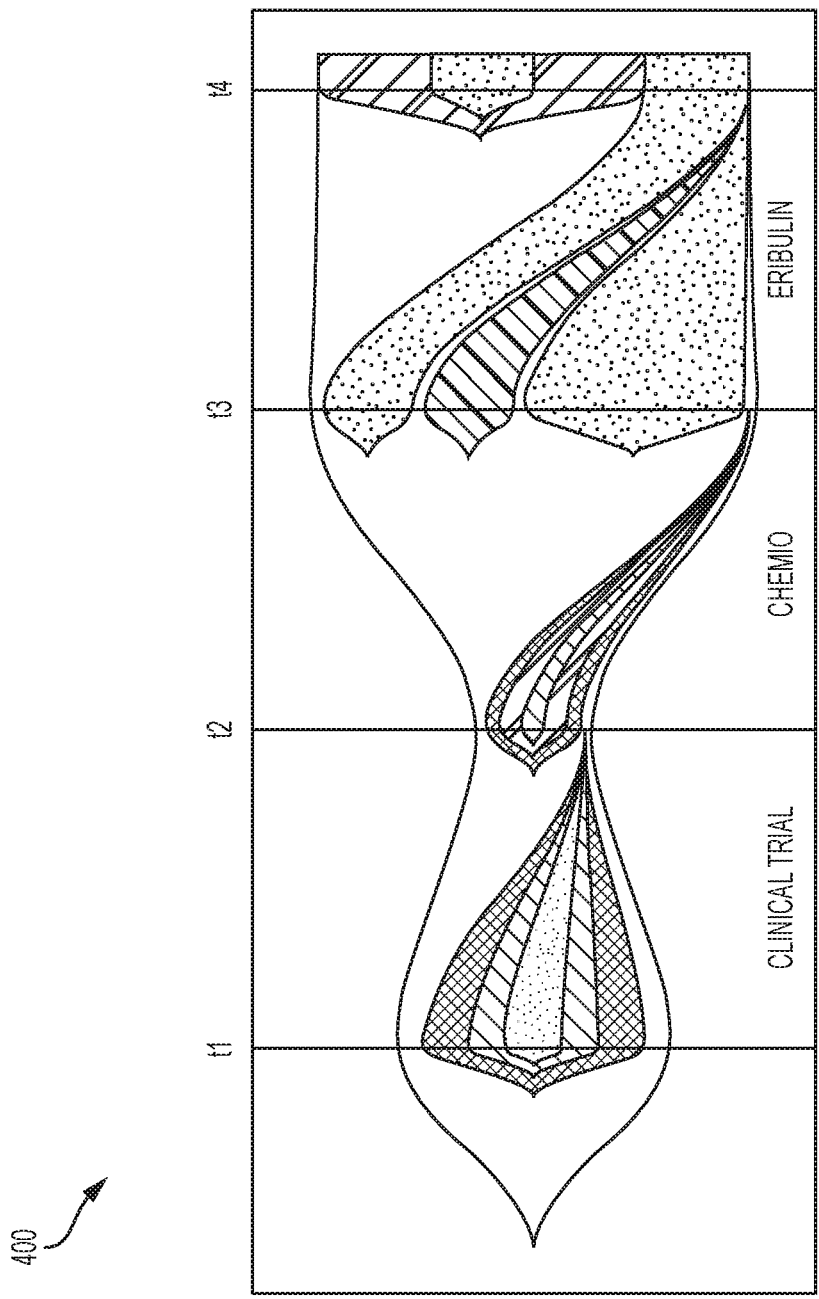
FIG. 4 depicts a Fishplot plot representation of the tumor evolution according to the tumor evolution tree of FIG. 3.

Consider the tumor of breast cancer patient 1 with four time points, that is, K=4. Specifically, FIG. 3 illustrates a δ-compliant time series tumor evolution tree 300 (specifically an MDT) with time point-specific clones 301-320, and with treatments 341-344 and treatment responses 350-354 indicated. In the tree of FIG. 3, the clones 301-320 have the following frequencies: 301 (1.0), 302 (0.01), 303 (0.76), 304 (0.23), 305 (0.53), 306 (0.23), 307 (0.72), 308 (0.28), 309 (0.16), 310 (0.28), 311 (0.28), 312 (0.52), 313 (0.24), 314 (0.24), 315 (0.01), 316 (0.43), 317 (0.08), 318 (0.19), 319 (0.29) and 320 (0.52). Clone 301 is the root clone for the tree. A processor 750 executes a software application 756 (depicted in FIG. 7) to create the time series tumor evolution tree 300. This information can induce possible new treatment action for the patient itself or other patients with similar mutation patterns. A Fishplot is shown in FIG. 4 as a complementary representation of the data in FIG. 3.

The generated MDT tree of FIG. 3 highlights which combinations of mutations, i.e., clones, are sensitive to a given treatment. This information can be used for the treatment of future patients that also exhibit a similar clone and so treatment that is more likely to be beneficial can be applied sooner. In addition, the tree can be used to create a profile or set of clones that are responsive a given treatment, and thus with subsequent patients, it would be possible to identify the diversity of clones present and then develop a combination treatment regimen based on the response profiles of individual clones found in these trees.

Figure 5:
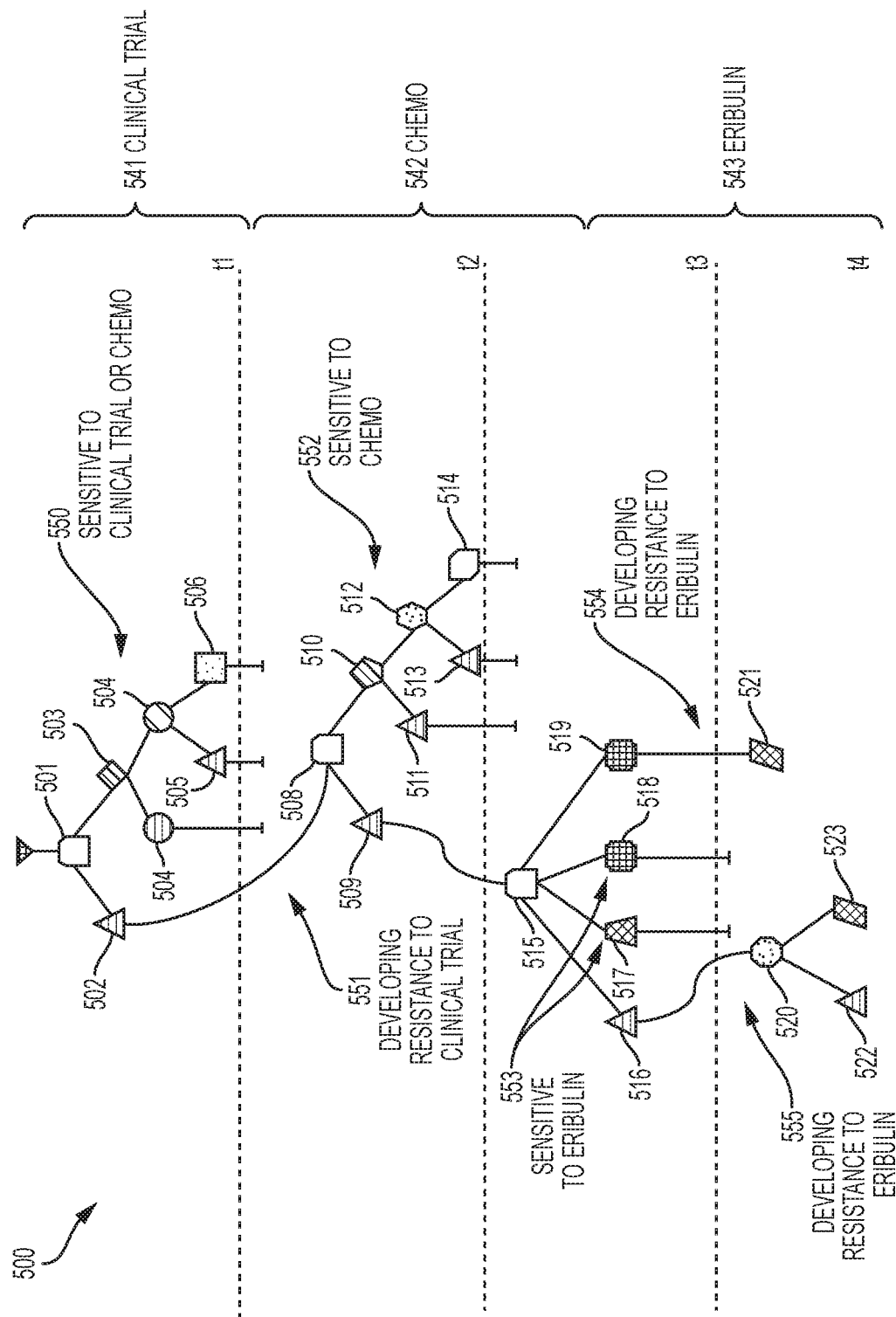
FIG. 5 depicts a tumor evolution tree with treatment information and likely points of resistance and sensitivity to treatments according to embodiments of the invention.
Figure 6:
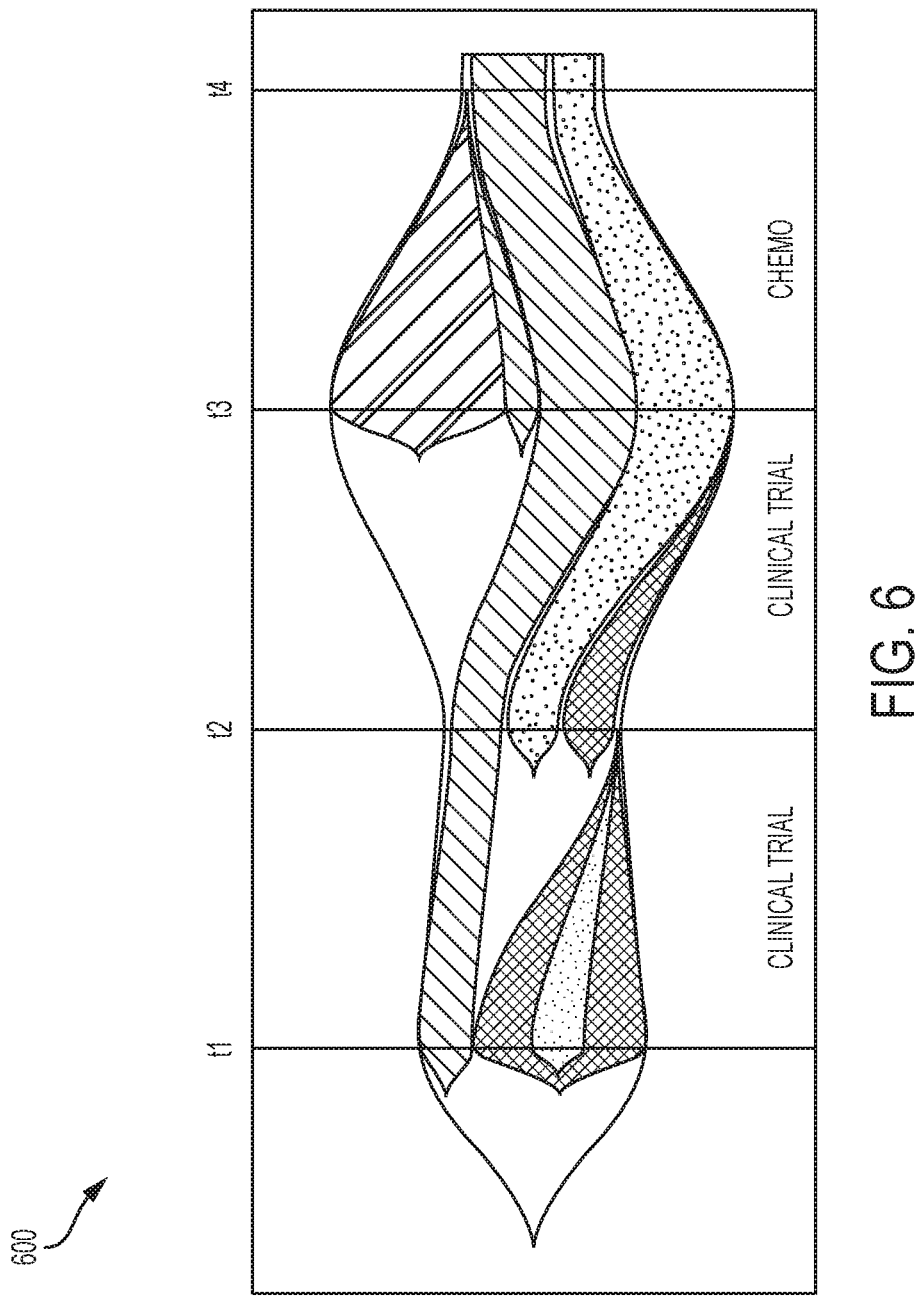
FIG. 6 depicts a Fishplot plot representation of the tumor evolution according to the tumor evolution tree of FIG. 5.

Consider also the tumor of breast cancer patient 2 with four time points, that is, K=4. Specifically, FIG. 5 illustrates a δ-compliant time series tumor evolution tree 500 (specifically an MDT) with time point-specific clones 501-523, and with treatments 541-543 and treatment responses 550-555 indicated. In the tree of FIG. 5, the clones 501-523 have the following frequencies: 501 (1.0), 502 (0.19), 503 (0.81), 504 (0.34), 505 (0.47), 506 (0.26), 507 (0.21), 508 (1.0), 509 (0.16), 510 (0.84), 511 (0.26), 512 (0.58), 513 (0.27), 514 (0.31), 515 (1.0), 516 (0.11), 517 (0.49), 518 (0.20), 519 (0.20), 520 (0.76), 521 (0.24), 522 (0.46) and 523 (0.30). Clone 501 is the root clone for the tree. A processor 750 executes a software application 756 (depicted in FIG. 7) to create the time series tumor evolution tree 300. This information can induce possible new treatment action for the patient itself or other patients with similar mutation patterns. A Fishplot is shown in FIG. 6 as a complementary representation of the data in FIG. 5.

The tree of FIG. 5 is similar to that of FIG. 3 except for this patient, there is a greater complexity in the per time point subgraphs $T_k$.

In an aspect of the invention, the subject's cancer treatment includes radiation therapy, surgery, chemotherapy, targeted therapy, hormone therapy, immunotherapy, stem cell transplant, or a combination including at least one of the foregoing.

In an aspect of the invention, determining by the processor, a further treatment for the subject, includes comparing the time series evolution tree composition with a database determined from a plurality of tumors from a plurality of subjects.

In another aspect of the invention, the further treatment includes a signal transduction pathway inhibitor, an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination including one or more of the foregoing.

More specifically, further treatment thus include signal transduction pathway inhibitors (e.g., ErbB inhibitors, EGFR inhibitors such as erlotinib), antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophosphamide, melphalan, biochoroethylnitrosurea, hydroxyurea), nitrogen mustards, (e.g., mechloethamine, melphan, chlorambucil, cyclophosphamide and Ifosfamide); nitrosoureas (e.g., carmustine, lomustine, semustine and streptozocin), platinum agents (e.g., cisplatin, carboplatin, oxaliplatin, JM-216, C 1-973), anthracyclines (e.g., doxrubicin, daunorubicin), antibiotics (e.g., mitomycin, idarubicin, adriamycin, daunomycin), topoisomerase inhibitors (e.g., etoposide, camptothecins), alkyl sulfonates including busulfan; triazines (e.g., dacarbazine); ethyenimines (e.g., thiotepa and hexamethylmelamine); folic acid analogs (e.g., methotrexate); pyrimidine analogues (e.g., 5 fluorouracil, cytosine arabinoside); purine analogs (e.g., 6-mercaptopurine, 6-thioguanine); antitumor antibiotics (e.g., actinomycin D; bleomycin, mitomycin C and methramycin); hormones and hormone antagonists (e.g., tamoxifen, cortiosteroids), anti-angiogenic agents (bevacizumab, endostatin and angiostatin), immunotherapeutic agents (transfection with cytokines such as interleukin 2, interleukin 4 or granulocyte-macrophage colony stimulating factor), cell cycle signaling inhibitors (CDK2, CDK4, and CDK6 inhibitors) and any other cytotoxic agents, (e.g., estramustine phosphate, prednimustine).

For example, signal transduction inhibitors include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes. Growth factor receptor tyrosine kinases include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Tyrosine kinases, which are not growth factor receptor kinases are termed non-receptor tyrosine kinases. Non-receptor tyrosine kinases include cSrc, Lck, Fyn, Yes, Jak, cAbl, FAK (Focal adhesion kinase), Brutons tyrosine kinase, and Bcr-Abl.

Inhibitors of Serine/Threonine Kinases include MAP kinase cascade blockers which include blockers of Raf kinases (rafk), Mitogen or Extracellular Regulated Kinase (MEKs), and Extracellular Regulated Kinases (ERKs); and the Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases.

Inhibitors of Phosphotidyl inositol-3 Kinase family members including blockers of PI3-kinase, ATM, DNA-PK, and Ku.

Inhibitors of Ras Oncogene include inhibitors of farnesyltransferase, geranyl-geranyl transferase, and CAAX proteases as well as anti-sense oligonucleotides, ribozymes and immunotherapy.

Alkylating agents alkylate molecules such as proteins, RNA and DNA and can covalently bind these molecules.

Alkylating agents affect any point in the cell cycle and thus are known as cell cycle-independent drugs.

Antimetabolites impede DNA and RNA synthesis.

Anti-microtubule agents block cell division by preventing microtubule function.

The method can include administering the further treatment to the subject. In an aspect, a computer-implemented method (e.g., by the processor 756 executing software 756 of computer system 702), includes the following steps. First the method includes inputting, to a processor, an N×K SSV frequency matrix M and a $\delta$, wherein $\delta \geq 0$ and is an error tolerance, wherein N is a number of SSVs and K is a number of time points, and wherein matrix M includes a plurality of time-resolved mutation frequencies for each of the SSVs, wherein each mutation frequency is between 0 and 1, and wherein the SSVs, the time points and the frequencies are based on sequence data for a tumor from a subject, and wherein at least one time-point represents an event in the subject's cancer treatment. Next the method includes clustering, by the processor, matrix rows in the matrix M that satisfy the $\delta$ to provide a plurality of SSV clusters, wherein each SSV cluster includes a plurality of SSVs with time-resolved mutation frequencies satisfying the $\delta$ Then the method includes assigning, by the processor, a mean cluster frequency to each SSV within each SSV cluster, to provide a first modified matrix M' including the mean cluster frequency for each SSV at each time point.

Then the method includes removing, by the processor, rows of the first modified matrix M' with cluster patterns across time points less than 1% to provide second modified matrix M", and calculating, by the computer, an $Err_{rare}$, wherein $Err_{rare}$ is the error introduced by the removing.

The method then includes scanning, by the processor, second modified matrix M" and for each row having one cell with a mean cluster frequency of 0, setting the entire row to 0, and calculating, by the computer, an $Err_{death}$, wherein $Err_{death}$ is the error introduced by setting rows to 1. The method then includes determining, by the processor, the maximum of $Err_{rare}$, $Err_{sweep}$, and $Err_{death}$ to provide $Err_{pre}$. The method then includes assigning, by the processor, for all SSV clusters of frequency 1 in the second modified matrix M", a root node. The method then includes calculating, by the processor, a $\delta$-compliant time-series evolution tree with an error $\leq \delta$ including the root node and a plurality time-stratified nodes, wherein the root node corresponds to time zero and each time-stratified node corresponds to a unique time point between 1 and K, by assigning, by the processor, for a time point j of the K time points, wherein $1 \leq j' < j$ and $j=1$ to K, a clonal configuration to each SSV cluster within time point j in second modified matrix M", wherein the clonal configuration for time point j has continuity with a clonal configuration for each SSV cluster within time point j' in second modified matrix M", and wherein the clonal configurations for time points j and j' do not include splitting of SSV clusters, identifying, by the processor, a set of SSV clusters having a mean cluster frequency of 0 at time point j' and randomly selecting, by the computer, a subset of the SSV clusters having a mean cluster frequency of 0 at time point j' and computing, by the processor, a re-configured clonal configuration for an error the clonal configurations for time points j and j' greater than $\delta$, and repeating, by the processor, until the $\delta$-compliant time-series evolution tree with an error $\leq \delta$ is determined, by the processor, from the re-configured clonal configuration, and calculating an $Err_j$ if a re-configured clonal configuration was computed, or computing, by the processor, the $\delta$-compliant time-series evolution tree from the clonal configurations for time points j and j' tree when the error ≤δ, and calculating, by the processor an $Error_{tree}=\max(Err_j, Err_{pre})$ for the δ-compliant time-series evolution tree. The method finally includes outputting, by the processor, the δ-compliant time-series evolution tree and corresponding $Error_{tree}$.

In an aspect, assigning, by the processor, for a time point j of the K time points a clonal configuration to each SSV cluster within time point j in second modified matrix M" is done using the Greedy algorithm.

In another aspect, the δ-compliant time-series evolution tree is a time-series evolution tree that has the smallest number of leaf nodes of the re-configured clonal configurations.

In yet another aspect, the method further includes assuming that each SSV is irreversible and unique, assuming that each SSV belongs to only one edge label on a path from the root node to the time-stratified node, assuming that the SSVs are independent and identically distributed, or a combination thereof.

In a still further aspect, the method further includes assuming that a sum of the frequencies for each of the SSV clusters in the plurality time-stratified nodes is not more than the frequency of a parent node; assuming that each node maps to a unique time-point; assuming that each set of subgraphs for any given time point sums to 1; or a combination thereof.

In any of the methods described herein, the mutation frequency is the cancer cell fraction (CCF) or the variant allele frequency (VAF).

In any of the methods described herein, the subject's cancer treatment includes radiation therapy, surgery, chemotherapy, targeted therapy, hormone therapy, immunotherapy, stem cell transplant, or a combination including at least one of the foregoing.

The methods can further include, determining, by the processor, an output for the subject based upon the δ-compliant time-series evolution tree. Exemplary outputs include that the subject is responding or not responding to a treatment based on the δ-compliant time-series evolution tree, determining a further clinical treatment for the subject based on the δ-compliant time-series evolution tree, or determining a time to obtain additional sequence data based on the δ-compliant time-series evolution tree. Optionally, the further treatment is administered to the subject.

From trees developed across many subjects, patterns as to what sequence of clonal population growth and death are associated to given treatments can be identified. From these patterns, the processor can determine to start, stop or change treatments to obtain the best result for the subject. A physician can administer the treatment determined by the computer. For example, it can be determined that often in response to eribulin, a particular clone develops, but only when that clone reaches a frequency ≥0.4 the clone becomes resistant. The processor can determine to shift treatment to another therapy while the frequency is <0.4 to avoid that severely resistant state. This type of insight can only be made with the inventive evolutionary tree that can be strictly tied back to sample time where we can map the patient's clinical history to clonal evolution. So in that regard, this invention is important to determine outcomes for subjects based on their time-resolved tumor evolution trees. In addition, trees that map to the actual cell populations in the tumor by the method of the invention will more reliably be able to guide treatment decisions.

FIG. 7 depicts a system 700 according to embodiments of the invention. Network 701 and computer system 702 can be used to store and communicate sequence data for tumors from one or more subjects, to calculate a matrix of SSVs and frequencies, and to calculate a δ-compliant time series tumor evolution tree. Also using the computer-implemented process, the time series evolution tree (e.g., 300 in FIG. 3) is used to make a treatment decision 706 which can then be administered to a patient. The computer system 702 includes one or more processors 750, memory 752, and one or more software applications 756 having computer-executable instructions to function as discussed herein. The processors 750 are configured to the execute computer-executable instructions of the software applications 756.

Figure 9:
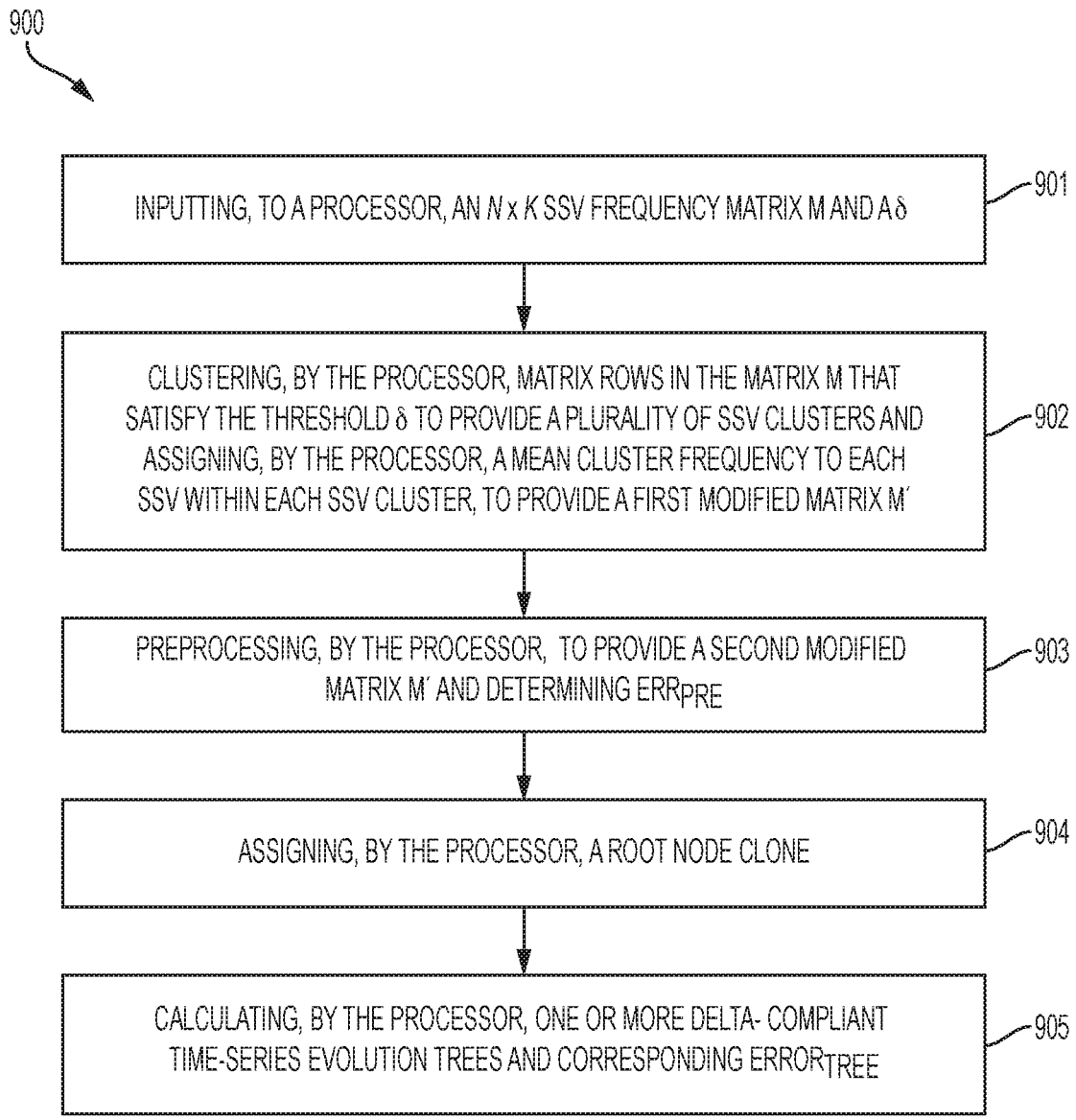
FIG. 9 is a flowchart of a computer-implemented method for constructing a time series tumor evolution tree according to embodiments of the present invention.

FIG. 9 is a flowchart of a computer-implemented method 900 by computer system 702 for constructing δ-compliant time series tumor evolution trees according to embodiments of the present invention. At block 901, an N×K SSV frequency matrix M and a δ are inputted to the computer system 702. At block 902, matrix rows in the matric M are clustered that satisfy the threshold δ to provide a plurality of SSV clusters (by the computer system 702) and then a mean cluster frequency is assigned to each SSV within each SSV cluster to provide modified matric M' (by the computer system 702). At block 903, preprocessing by the computer system 702 provides a second modified matric M" and an $Err_{pre}$. At block 904, root node clone is assigned (by the computer system 702). And at block 905, a δ-compliant time series tumor evolution tree and $Error_{tree}$ are calculated by the computer system 702.

Figure 10:
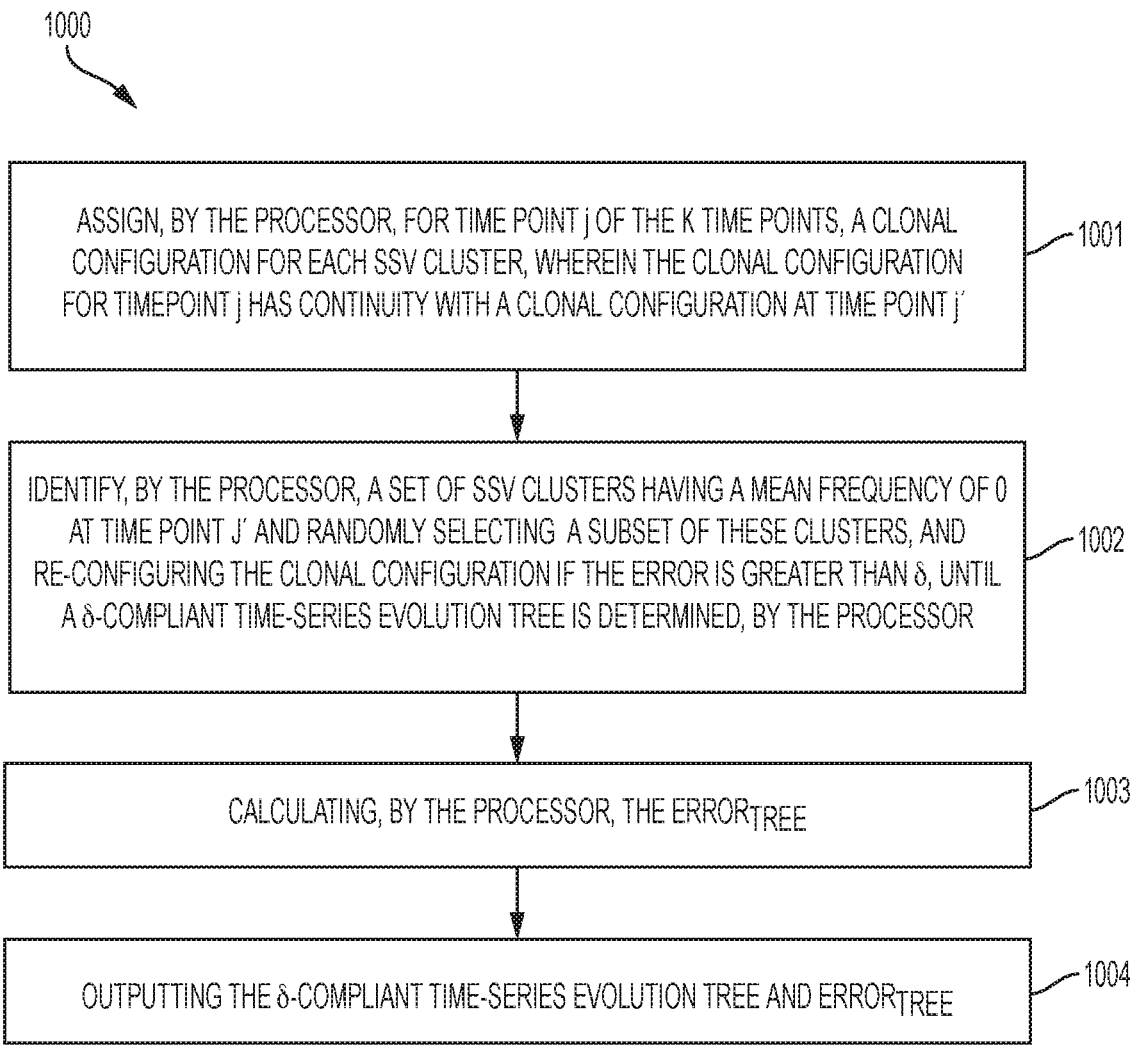
FIG. 10 is a flowchart of calculating a δ-compliant time series evolution tree according to embodiments of the present invention.

FIG. 10 is a flowchart of the computer-implemented method 1000 by computer system 702 for calculating δ-compliant time series tumor evolution trees according to embodiments of the present invention. At block 1001, a clonal configuration is assigned, by the processor, for time point j of the K time points and a clonal configuration for the SSV clusters is determined. The clonal configuration for time point j has continuity with a clonal configuration at time point j'. At block 1002, a set of SSV clusters having a mean frequency of 0 at time point j' is identified by the processor. The processor randomly selects a subset of these clusters and the clonal configuration is re-configured if the error is greater than δ. Reconfiguration is continued until a δ-complaint time-series evolution tree is determined by the processor. At block 1003, the $Error_{tree}$ is determined by the processor. An at block 1004, the processor outputs the δ-complaint time-series evolution tree and the $Error_{tree}$.

Figure 11:
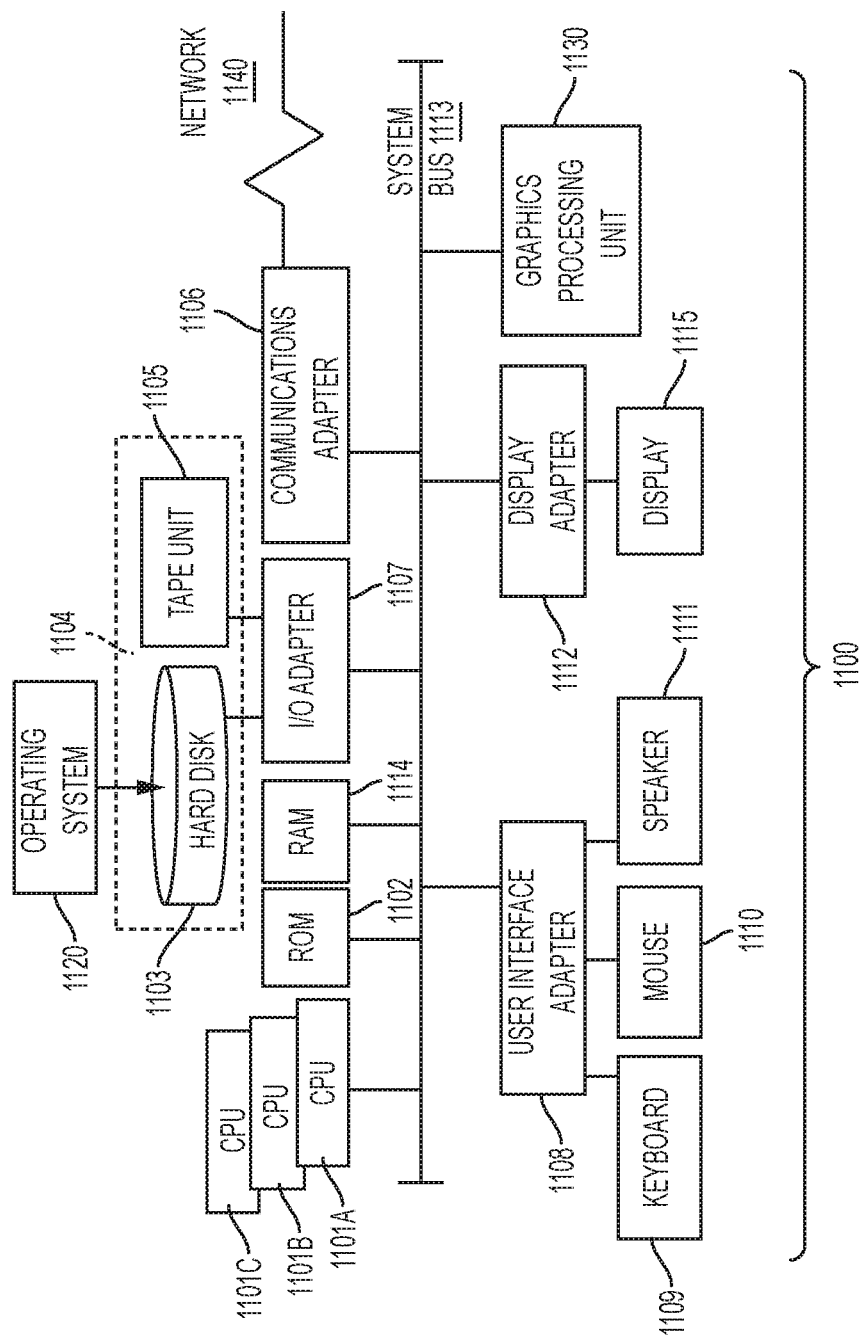
FIG. 11 depicts a computer/processing system having components and/or functionality for practicing one or more embodiments of the present invention.

FIG. 11 depicts exemplary components of a computer system 1100 according to one or more embodiments of the present invention. Any of the elements and functionality of computer system 1100 can be included in any of the elements in FIGS. 1-10. Particularly, computer system 702 can implement the elements of computer system 1100 to perform the functions discussed herein. The computer system 700 is a processing system. The processing system 1100 can include one or more central processing units (processors) 1101A, 1101B, 1101C, etc. (collectively or generically referred to as processor(s) 1101). In one or more embodiments, each processor 1101 can include a reduced instruction set computer (RISC) microprocessor. Processors 1101 are coupled to system memory 1114 and various other components via a system bus 1113. Read only memory (ROM) 1102 is coupled to the system bus 1113 and can include a basic input/output system (BIOS), which controls certain basic functions of processing system 700.

FIG. 11 further depicts an input/output (I/O) adapter 1107 and a network adapter 1106 coupled to the system bus 1113. I/O adapter 1107 can be a small computer system interface (SCSI) adapter that communicates with a hard disk 1103 and/or tape storage drive 1105 or any other similar component. I/O adapter 1107, hard disk 1103, and tape storage device 1105 are collectively referred to herein as mass storage 1104. Operating system 1120 for execution on the processing system 1100 can be stored in mass storage 1104. The network adapter 1106 interconnects bus 1113 with an outside network, for example, network 1140, enabling data processing system 1100 to communicate with other such systems. A screen (e.g., a display monitor) 1115 is connected to system bus 1113 by display adaptor 1112, which can include a graphics adapter to improve the performance of graphics intensive applications and a video controller. In one or more embodiments of the present invention, adapters 1107, 1106, and 1112 can be connected to one or more I/O busses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 1113 via user interface adapter 1108 and display adapter 1112. A keyboard 1109, mouse 1110, and speaker 1111 all interconnected to bus 1113 via user interface adapter 1108, which can include, for example, a Super I/O chip integrating multiple device adapters into a single integrated circuit.

In exemplary embodiments, the processing system 1100 includes a graphics processing unit 1130. Graphics processing unit 1130 is a specialized electronic circuit designed to manipulate and alter memory to accelerate the creation of images in a frame buffer intended for output to a display. In general, graphics processing unit 1130 is very efficient at manipulating computer graphics and image processing and has a highly parallel structure that makes it more effective than general-purpose CPUs for algorithms where processing of large blocks of data is done in parallel.

Thus, as configured in FIG. 11, the processing system 1100 includes processing capability in the form of processors 1101, storage capability including system memory 1114 and mass storage 1104, input means such as keyboard 1109 and mouse 1110, and output capability including speaker 1111 and display 1115. In one implementation, a portion of system memory 1114 and mass storage 1104 collectively store an operating system coordinate the functions of the various components shown in FIG. 11.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   inputting, to a processor, an N×K SSV frequency matrix M and a $\delta$, wherein $\delta \geq 0$ and is an error tolerance, wherein N is a number of SSVs and K is a number of time points, and wherein matrix M comprises a plurality of time-resolved mutation frequencies for each of the SSVs, wherein each mutation frequency is between 0 and 1, and wherein the SSVs, the time points and the frequencies are based on sequence data for a tumor from a subject, and wherein at least one time-point represents an event in the subject's cancer treatment;
   clustering, by the processor, matrix rows in the matrix M that satisfy the $\delta$ to provide a plurality of SSV clusters, wherein each SSV cluster comprises a plurality of SSVs with time-resolved mutation frequencies satisfying the $\delta$;
   assigning, by the processor, a mean cluster frequency to each SSV within each SSV cluster, to provide a first modified matrix M' comprising the mean cluster frequency for each SSV at each time point;
   removing, by the processor, rows of the first modified matrix M' with cluster patterns across time points less than 1% to provide second modified matrix M", and calculating, by the computer, an $\text{Err}_{rare}$, wherein $\text{Err}_{rare}$ is the error introduced by the removing;
   scanning, by the processor, second modified matrix M" and for each row having one cell with a mean cluster frequency of 1, setting the entire row to 1, and calculating, by the computer, an $\text{Err}_{sweep}$, wherein $\text{Err}_{sweep}$ is the error introduced by setting rows to 1;
   scanning, by the processor, second modified matrix M" and for each row having one cell with a mean cluster frequency of 0, setting the entire row to 0, and calculating, by the computer, an $\text{Err}_{death}$, wherein $\text{Err}_{death}$ is the error introduced by setting rows to 1;
   determining, by the processor, the maximum of $\text{Err}_{rare}$, $\text{Err}_{sweep}$, and $\text{Err}_{death}$ to provide $\text{Err}_{pre}$;
   assigning, by the processor, for all SSV clusters of frequency 1 in the second modified matrix M", a root node;
   calculating, by the processor, a $\delta$-compliant time-series evolution tree with an error $\leq \delta$ comprising the root node and a plurality time-stratified nodes, wherein the root node corresponds to time zero and each time-stratified node corresponds to a unique time point between 1 and K, by:
   assigning, by the processor, for a time point j of the K time points, wherein $1 \leq j' < j$ and j=1 to K, a clonal configuration to each SSV cluster within time point j in second modified matrix M", wherein the clonal configuration for time point j has continuity with a clonal configuration for each SSV cluster within time point j' in second modified matrix M", and wherein the clonal configurations for time points j and j' do not include splitting of SSV clusters;
   identifying, by the processor, a set of SSV clusters having a mean cluster frequency of 0 at time point j' and randomly selecting, by the computer, a subset of the SSV clusters having a mean cluster frequency of 0 at time point j'; and
   computing, by the processor, a re-configured clonal configuration for an error the clonal configurations for time points j and j' greater than $\delta$, and repeating, by the processor, until the $\delta$-compliant time-series evolution tree with an error $\leq \delta$ is determined, by the processor, from the re-configured clonal configuration, and calculating an $\text{Err}_j$ if a re-configured clonal configuration was computed; or
   computing, by the processor, the $\delta$-compliant time-series evolution tree from the clonal configurations for time points j and j' tree when the error $\leq \delta$; and
   calculating, by the processor an $\text{Error}_{tree} = \max(\text{Err}_j, \text{Err}_{pre})$ for the $\delta$-compliant time-series evolution tree; and
   outputting, by the processor, the $\delta$-compliant time-series evolution tree and corresponding $\text{Error}_{tree}$.

2. The computer-implemented method of claim 1, wherein assigning, by the processor, for a time point j of the K time points a clonal configuration to each SSV cluster within time point j in second modified matrix M" is done using the Greedy algorithm.

3. The computer-implemented method of claim 1, wherein the δ-compliant time-series evolution tree a time-series evolution tree has the smallest number of leaf nodes of the re-configured clonal configurations.

4. The computer-implemented method of claim 1, further comprising assuming that each SSV is irreversible and unique, assuming that each SSV belongs to only one edge label on a path from the root node to the time-stratified node, assuming that the SSVs are independent and identically distributed, or a combination thereof.

5. The computer-implemented method of claim 1, further comprising assuming that a sum of the frequencies for each of the SSV clusters in the plurality time-stratified nodes is not more than the frequency of a parent node; assuming that each node maps to a unique time-point; assuming that each set of subgraphs for any given time point sums to 1; or a combination thereof.

6. The computer-implemented method of claim 1, wherein the mutation frequency is the cancer cell fraction (CCF) or the variant allele frequency (VAF).

7. The computer-implemented method of claim 1, wherein the subject's cancer treatment comprises radiation therapy, surgery, chemotherapy, targeted therapy, hormone therapy, immunotherapy, stem cell transplant, or a combination comprising at least one of the foregoing.

8. The computer-implemented method of claim 1, further comprising determining an outcome for the subject based upon the δ-compliant time-series evolution tree.

9. The computer-implemented method of claim 8, wherein the outcome comprises determining, by the processor, that the subject is responding or not responding to a treatment based on the δ-compliant time-series tumor evolution tree, determining a further clinical treatment for the subject based on the δ-compliant time-series tumor evolution tree, or determining a time to obtain additional sequence data based on the δ-compliant time-series tumor evolution tree.

10. The computer-implemented method of claim 9, further comprising administering the further clinical treatment to the subject.

11. A computer program product for cancer treatment, the computer program product comprising a computer readable storage medium having program instructions embodied therewith, the program instructions executable by a processor to cause the processor to perform operations comprising:
inputting, to the processor, an N×K SSV frequency matrix M and a δ, wherein δ≥0 and is an error tolerance, wherein N is a number of SSVs and K is a number of time points, and wherein matrix M comprises a plurality of time-resolved mutation frequencies for each of the SSVs, wherein each mutation frequency is between 0 and 1, and wherein the SSVs, the time points and the frequencies are based on sequence data for a tumor from a subject, and wherein at least one time-point represents an event in the subject's cancer treatment;
clustering, by the processor, matrix rows in the matrix M that satisfy the δ to provide a plurality of SSV clusters, wherein each SSV cluster comprises a plurality of SSVs with time-resolved mutation frequencies satisfying the δ;
assigning, by the processor, a mean cluster frequency to each SSV within each SSV cluster, to provide a first modified matrix M' comprising the mean cluster frequency for each SSV at each time point;
removing, by the processor, rows of the first modified matrix M' with cluster patterns across time points less than 1% to provide second modified matrix M", and calculating, by the computer, an $Err_{rare}$, wherein $Err_{rare}$ is the error introduced by the removing;
scanning, by the processor, second modified matrix M" and for each row having one cell with a mean cluster frequency of 1, setting the entire row to 1, and calculating, by the computer, an $Err_{sweep}$, wherein $Err_{sweep}$ is the error introduced by setting rows to 1;
scanning, by the processor, second modified matrix M" and for each row having one cell with a mean cluster frequency of 0, setting the entire row to 0, and calculating, by the computer, an $Err_{death}$, wherein $Err_{death}$ is the error introduced by setting rows to 1;
determining, by the processor, the maximum of $Err_{rare}$, $Err_{sweep}$, and $Err_{death}$ to provide $Err_{pre}$;
assigning, by the processor, for all SSV clusters of frequency 1 in the second modified matrix M", a root node;
calculating, by the processor, a δ-compliant time-series evolution tree with an error ≤δ comprising the root node and a plurality time-stratified nodes, wherein the root node corresponds to time zero and each time-stratified node corresponds to a unique time point between 1 and K, by
assigning, by the processor, for a time point j of the K time points, wherein 1≤j'<j and j=1 to K, a clonal configuration to each SSV cluster within time point j in second modified matrix M", wherein the clonal configuration for time point j has continuity with a clonal configuration for each SSV cluster within time point j' in second modified matrix M", and wherein the clonal configurations for time points j and j' do not include splitting of SSV clusters,
identifying, by the processor, a set of SSV clusters having a mean cluster frequency of 0 at time point j' and randomly selecting, by the computer, a subset of the SSV clusters having a mean cluster frequency of 0 at time point j', and
computing, by the processor, a re-configured clonal configuration for an error the clonal configurations for time points j and j' greater than δ, and repeating, by the processor, until the δ-compliant time-series evolution tree with an error ≤δ is determined, by the processor, from the re-configured clonal configuration, and calculating an $Err_j$ if a re-configured clonal configuration was computed, or
computing, by the processor, the δ-compliant time-series evolution treefrom the clonal configurations for time points j and j' tree when the error ≤δ, and
calculating, by the processor an $Error_{tree}=\max(Err_j, Err_{pre})$ for the δ-compliant time-series evolution tree; and
outputting, by the processor, the δ-compliant time-series evolution tree and corresponding $Error_{tree}$.

12. The computer program product for cancer treatment of claim 11, wherein the δ-compliant time-series evolution tree a time-series evolution tree has the smallest number of leaf nodes of the re-configured clonal configurations.

13. The computer program product for cancer treatment of claim 11, wherein the subject's cancer treatment comprises radiation therapy, surgery, chemotherapy, targeted therapy, hormone therapy, immunotherapy, stem cell transplant, or a combination comprising at least one of the foregoing.

14. The computer program product for cancer treatment of claim 11, further comprising determining an outcome for the subject based upon the δ-compliant time series evolution tree.

15. The computer program product for cancer treatment of claim 11, wherein the outcome comprises determining, by the processor, that the subject is responding or not responding to a treatment based on the δ-compliant time-series tumor evolution tree, determining a further clinical treatment for the subject based on the δ-compliant time-series tumor evolution tree, or determining a time to obtain additional sequence data based on the δ-compliant time-series tumor evolution tree.

16. A computer system for generating a cancer treatment methodology, the compute system comprising:
a processor; and
a computer readable storage medium storing executable instructions that, when executed by the processor, cause the processor to perform operations comprising:
  inputting, to a processor, an N×K SSV frequency matrix M and a δ, wherein δ≥0 and is an error tolerance, wherein N is a number of SSVs and K is a number of time points, and wherein matrix M comprises a plurality of time-resolved mutation frequencies for each of the SSVs, wherein each mutation frequency is between 0 and 1, and wherein the SSVs, the time points and the frequencies are based on sequence data for a tumor from a subject, and wherein at least one time-point represents an event in the subject's cancer treatment;
  clustering, by the processor, matrix rows in the matrix M that satisfy the δ to provide a plurality of SSV clusters, wherein each SSV cluster comprises a plurality of SSVs with time-resolved mutation frequencies satisfying the δ;
  assigning, by the processor, a mean cluster frequency to each SSV within each SSV cluster, to provide a first modified matrix M' comprising the mean cluster frequency for each SSV at each time point;
  removing, by the processor, rows of the first modified matrix M' with cluster patterns across time points less than 1% to provide second modified matrix M", and calculating, by the computer, an $\text{Err}_{rare}$, wherein $\text{Err}_{rare}$ is the error introduced by the removing;
  scanning, by the processor, second modified matrix M" and for each row having one cell with a mean cluster frequency of 1, setting the entire row to 1, and calculating, by the computer, an $\text{Err}_{sweep}$, wherein $\text{Err}_{sweep}$ is the error introduced by setting rows to 1;
  scanning, by the processor, second modified matrix M" and for each row having one cell with a mean cluster frequency of 0, setting the entire row to 0, and calculating, by the computer, an $\text{Err}_{death}$, wherein $\text{Err}_{death}$ is the error introduced by setting rows to 1;
  determining, by the processor, the maximum of $\text{Err}_{rare}$, $\text{Err}_{sweep}$, and $\text{Err}_{death}$ to provide $\text{Err}_{pre}$;
  assigning, by the processor, for all SSV clusters of frequency 1 in the second modified matrix M", a root node;
  calculating, by the processor, a δ-compliant time-series evolution tree with an error ≤δ comprising the root node and a plurality time-stratified nodes, wherein the root node corresponds to time zero and each time-stratified node corresponds to a unique time point between 1 and K, by
  assigning, by the processor, for a time point j of the K time points, wherein 1≤j'<j and j=1 to K, a clonal configuration to each SSV cluster within time point j in second modified matrix M", wherein the clonal configuration for time point j has continuity with a clonal configuration for each SSV cluster within time point j' in second modified matrix M", and wherein the clonal configurations for time points j and j' do not include splitting of SSV clusters,
  identifying, by the processor, a set of SSV clusters having a mean cluster frequency of 0 at time point j' and randomly selecting, by the computer, a subset of the SSV clusters having a mean cluster frequency of 0 at time point j', and
  computing, by the processor, a re-configured clonal configuration for an error the clonal configurations for time points j and j' greater than δ, and repeating, by the processor, until the δ-compliant time-series evolution tree with an error ≤δ is determined, by the processor, from the re-configured clonal configuration, and calculating an $\text{Err}_j$ if a re-configured clonal configuration was computed, or
  computing, by the processor, the δ-compliant time-series evolution tree from the clonal configurations for time points j and j' tree when the error ≤δ, and
  calculating, by the processor an $\text{Error}_{free}=\max(\text{Err}_j, \text{Err}_{pre})$ for the δ-compliant time-series evolution tree; and
  outputting, by the processor, the δ-compliant time-series evolution tree and corresponding $\text{Error}_{tree}$.

17. The system of claim 16, wherein the δ-compliant time-series evolution tree a time-series evolution tree has the smallest number of leaf nodes of the re-configured clonal configurations.

18. The system of claim 16, wherein the subject's cancer treatment comprises radiation therapy, surgery, chemotherapy, targeted therapy, hormone therapy, immunotherapy, stem cell transplant, or a combination comprising at least one of the foregoing.

19. The system of claim 16, further comprising determining an outcome for the subject based upon the δ-compliant time-series evolution tree.

20. The system of claim 16, wherein the outcome comprises determining, by the processor, that the subject is responding or not responding to a treatment based on the δ-compliant time-series tumor evolution tree, determining a further clinical treatment for the subject based on the δ-compliant time-series tumor evolution tree, or determining a time to obtain additional sequence data based on the δ-compliant time-series tumor evolution tree.

* * * * *